(12) United States Patent
Yuan et al.

(10) Patent No.: US 10,281,377 B1
(45) Date of Patent: May 7, 2019

(54) SAMPLE LOADING APPARATUS FOR LASER ABLATION

(71) Applicant: Northwest University, Xi'an, Shaanxi (CN)

(72) Inventors: Honglin Yuan, Shaanxi (CN); Kaiyun Chen, Shaanxi (CN); Zhian Bao, Shaanxi (CN)

(73) Assignee: Northwest University, Xi'an (CN)

( * ) Notice: Subject to any disclaimer, the term of this patent is extended or adjusted under 35 U.S.C. 154(b) by 0 days.

(21) Appl. No.: 15/942,520

(22) Filed: Mar. 31, 2018

(30) Foreign Application Priority Data

Mar. 19, 2018 (CN) .......................... 2018 1 0222698

(51) Int. Cl.
*G01N 1/44* (2006.01)
*H01J 49/04* (2006.01)
(Continued)

(52) U.S. Cl.
CPC .............. *G01N 1/44* (2013.01); *G01N 21/718* (2013.01); *H01J 49/0422* (2013.01); *H01J 49/161* (2013.01)

(58) Field of Classification Search
CPC ........... G01N 15/1404; G01N 15/1484; G01N 2015/1006; G01N 2015/1481; G01N 2015/149; G01N 2333/91205; G01N 2800/52; G01N 15/1434; G01N 15/1459; G01N 2015/0065; G01N 2015/0088; G01N 2015/1081; G01N 2015/1411; G01N 33/54366; G01N 35/08; G01N 2015/1493; G01N 33/15; G01N 33/5094; G01N 13/00; G01N 1/34; G01N 2013/003; G01N 2015/008; G01N 2021/6439; G01N 2030/77; G01N 2033/0093; G01N 2035/00158; G01N 2035/00881; G01N 21/6452; G01N 21/648; G01N 21/65; G01N 21/7703; G01N 2201/0221; G01N 2201/0612; G01N 2333/70596; G01N 27/44704; G01N 27/44791; G01N 27/624;
(Continued)

(56) References Cited

U.S. PATENT DOCUMENTS 3,652,170 A * 3/1972 Beer .................. G01N 35/1095
250/576
4,980,057 A * 12/1990 Dorn .................. G01N 30/7246
210/149
(Continued)

*Primary Examiner* — Michael P Stafira
(74) *Attorney, Agent, or Firm* — Wayne & Ken, LLC

(57) ABSTRACT

The present invention discloses a sample loading apparatus for laser ablation, including a target seat, a base, an air channel, an aerosol channel and a sample chamber, wherein a shrinking mouth is formed in the top of the sample chamber and positioned on a lower surface of the aerosol channel; a spring is arranged in the sample chamber; an opening is formed in a lower surface of the sample chamber and communicated with an air outlet; a stop valve is arranged at the air outlet; one end of the aerosol channel is communicated with a carrier gas inlet, and the other end is communicated with an aerosol outlet; and a top of the aerosol channel includes a first transparent material. The present invention increases stable reliability in a continuous use process, and improves consistency of aerosol transmission efficiency, so that different samples are analyzed.

10 Claims, 10 Drawing Sheets

(51) Int. Cl.
*H01J 49/16* (2006.01)
*G01N 21/71* (2006.01)

(58) Field of Classification Search
CPC .............. G01N 27/66; G01N 30/6069; G01N
30/6095; G01N 30/74; G01N 31/221;
G01N 33/0027; G01N 33/4833; G01N
33/48721; G01N 33/54373; G01N 33/60;
G01N 33/84; G01N 33/94; G02B 1/12;
G02B 26/0816; G02B 26/0833; G02B
5/0891; G02B 6/003; G02B 6/0095;
G02B 6/4291; G02B 7/1815; G02B
7/1821; G02B 7/1827; G02B 7/198
See application file for complete search history.

(56) References Cited

U.S. PATENT DOCUMENTS

| | | | | |
|---|---|---|---|---|
| 5,830,413 | A * | 11/1998 | Lang | G01N 1/312 |
| | | | | 422/563 |
| 6,188,474 | B1 * | 2/2001 | Dussault | G01N 21/0303 |
| | | | | 356/246 |
| 6,657,718 | B1 * | 12/2003 | Petersen | G01N 21/03 |
| | | | | 250/573 |
| 6,913,938 | B2 * | 7/2005 | Shanmugasundram | |
| | | | | C23C 16/52 |
| | | | | 257/E21.525 |
| 2001/0006417 | A1 * | 7/2001 | Modlin | B01L 3/50853 |
| | | | | 356/246 |
| 2010/0322997 | A1 * | 12/2010 | Enomura | A61K 9/0048 |
| | | | | 424/444 |
| 2014/0260621 | A1 * | 9/2014 | Gogol, Jr. | G01N 29/12 |
| | | | | 73/579 |

* cited by examiner

SAMPLE LOADING APPARATUS FOR LASER ABLATION

TECHNICAL FIELD

The present invention relates to the field of sample loading apparatuses, and particularly relates to a sample loading apparatus for laser ablation.

BACKGROUND

An in-situ laser analysis technology (including LIBS and LA-ICP-MS) is a technology capable of realizing in-situ sampling in a micron area, combines laser ablation and spectrum or plasma mass spectrometry and may realize analysis of content of primary trace elements or isotope composition in a sample. In recent years, the technology is widely applied to the fields of geoscience, modern science and technology archaeology, material science, bioscience and the like.

The in-situ laser analysis technology focuses the laser on a sample surface to ablate the sample by virtue of a light path, analyzes plasma generated by ablation to obtain an LIBS spectral signal, and conducts mass spectrometry on aerosol generated by ablation to obtain an ion signal; and the two signals may be complementary to each other, so that the content of the primary trace elements or the isotope composition is obtained to perform element distribution law or isotopic tracing, labeling and other studies, such as a study on a poisoning mechanism of heavy metals in animal brains and livers, a study on sources of heavy metal pollutants in soil, a study on element and isotopic geochemical tracing for formation and evolution of the earth, a history of civilization on element and isotope composition tracing in archaeological samples of bronze ware, ceramics and the like, etc.

In the in-situ laser analysis, a process that the laser acts on the sample is performed in a sample chamber, while key factors that influence the reliability of results of the in-situ laser analysis technology include a heat effect that acts on the sample surface by the laser in a process of ablating the sample by the laser, and an elemental fractionation effect caused by different ablation efficiencies of different elements/isotopes in the sample due to a transmission efficiency difference of the aerosol generated by ablation. The key factor that influences the stability of the results of the in-situ laser analysis technology includes instability of a subsequent plasma ion source caused by air (particularly oxygen) introduced in a sample replacement process. The heat effect of the laser may be solved by changing the pulse width of a laser device.

At present, a sample loading apparatus for laser ablation is generally as follows: a glass window through which the laser can pass is formed in a circular sample chamber, or a small inner chamber is formed in a larger sample chamber. The previous sample chamber has a small volume, and generally may simultaneously load one sample target and one standard target only. Moreover, if samples have different positions in the sample chamber, the aerosol transmission efficiency is often influenced and a severe fractionation effect is caused, thereby influencing accuracy of the analysis result. With respect to the latter sample chamber, since the main sample chamber is large and the small sample chamber is close to an upper side, air in the main sample chamber is difficult to be completely replaced with carrier gas (generally helium); and oxygen which is slowly released in the sample target and the carrier gas will be gradually accumulated in the main sample chamber, causing the gradual increase of spectral interference caused by the oxygen, so that baselines of partial elements are gradually elevated in the analysis process (e.g., a signal that $^{16}O^{16}O$ interferes with $^{32}S$, a signal that $^{16}O^{40}Ar$ interferes with $^{56}Fe$, and the like). A signal to noise ratio is influenced; analytical accuracy of the content of interfered elements and an isotope ratio is poor; and a detection limit is decreased. Therefore, it is necessary to improve the above defects.

SUMMARY

To overcome the above defects in the prior art, the present invention provides a sample loading apparatus for laser ablation capable of increasing transmission efficiency of aerosol generated by ablation, enhancing consistency of in-situ laser analysis conditions and enabling in-situ laser analysis results to be more stable and reliable. The present invention is realized by the following technical solution: the sample loading apparatus for laser ablation includes a sample chamber, a carrier gas inlet and a gas outlet and further includes a target seat and a base, wherein the gas outlet includes an air outlet and an aerosol outlet; the target seat and the base are connected hermetically and form an air channel, an aerosol channel and a sample chamber, wherein a shrinking mouth is formed in the top of the sample chamber and positioned in a lower surface of the aerosol channel;

a spring is arranged in the sample chamber and is used for enabling a sample target to be limited in the sample chamber and abutted at the shrinking mouth;

an opening is formed in a lower surface of the sample chamber and communicated with the air outlet by virtue of the air channel;

a stop valve is arranged at the air outlet and is used for opening and closing the air outlet; and one end of the aerosol channel is communicated with the carrier gas inlet, and the other end of the aerosol channel is communicated with the aerosol outlet; and the top of the aerosol channel includes a first transparent material, so that laser transmits from the top of the aerosol channel by virtue of the first transparent material and ablates the sample target.

Preferably, a porous screen guide plate is arranged at the carrier gas inlet, for guiding the carrier gas.

Preferably, a blocking sheet is arranged on the top of the sample chamber, and an opening is formed in the middle part of the blocking sheet to form the shrinking mouth.

Preferably, the carrier gas inlet and the aerosol outlet are respectively positioned on two opposite side surfaces of the target seat, the aerosol channel is positioned in the target seat, and a middle part of the aerosol channel is in the shape of a flat cuboid.

Preferably, the target seat includes an upper chamber body; the base includes a lower chamber body; one end of the spring is fixedly arranged on the lower chamber body; the target seat and the base are sealed by an O-shaped sealing ring; and the upper chamber body and the lower chamber body correspond to each other and form the sample chamber.

Preferably, the target seat includes a first transparent sheet and a first stepped groove; the first stepped groove is formed in a top surface of the target seat; the first transparent sheet is hermetically arranged at a notch of the first stepped groove; the first transparent sheet is formed by the first transparent material; and the first transparent material includes fluorite glass or UV transparent quartz glass.

Preferably, the base includes a second transparent sheet and a second stepped groove; the second stepped groove is formed in a bottom surface of the base; the second transparent sheet is hermetically arranged at a notch of the second stepped groove; the air channel is positioned in the base; and the air outlet is positioned in a side surface of the base.

Preferably, a volume of the aerosol channel is: 0 ml<V<5 ml; the sectional area of the aerosol channel is: 0 cm$^2$<S<0.5 cm$^2$; and a height from the top surface of the aerosol channel to the upper surface of the sample target is: 0.5 mm≤H≤3.0 mm.

Preferably, a shape of the shrinking mouth is matched with a shape of the sample target, so that the shrinking mouth is covered by the sample target.

Preferably, a quantity of the sample chambers is: 6≤N≤15, and the sample chambers are communicated in series by virtue of air channels.

According to the present invention, more than 6 sample targets may be simultaneously introduced; small laser ablation and the aerosol channel ensure that analytical detection limits and accuracy are not influenced due to elevation of mass spectrometry baselines caused by interference of oxygen and nitrogen after continuous operations in the sample chambers, and also ensure that transmission efficiencies of all the samples and standard aerosols are completely consistent, and the different samples are analyzed under the same analysis condition of the mass spectrometer; and influences on mass spectrometry reliability and analysis efficiency due to the changes of instrumental analysis conditions caused by the accumulation of interference in a traditional large sample chamber and repeated opening of small sample chambers for replacing the samples are eliminated.

BRIEF DESCRIPTION OF DRAWINGS

The present invention is further described below in detail in combination with drawings and specific embodiments.

Figure 1:
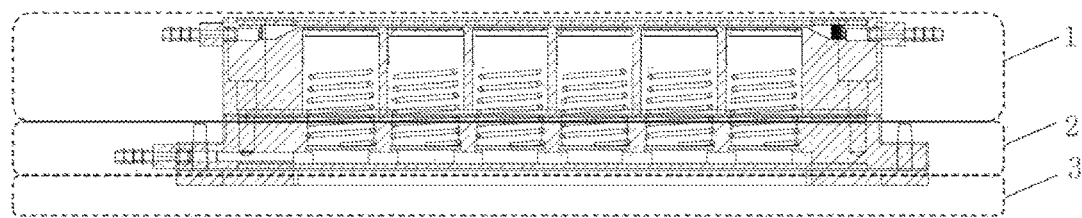
FIG. 1 is a schematic diagram of a longitudinal section structure of a no-load state in embodiments of the present invention.

Various numerals in the figures are as follows: target seat 1; base 2; adapter plate 3; first stepped groove 4; carrier gas inlet 5; porous screen guide plate 6; first end part 7; fixing piece 8; second end part 9; aerosol outlet 10; aerosol channel 11; blocking sheet 12; upper chamber body 13; fixing hole 14; fixing hole 15; lower chamber body 16; supporting piece 17; second shrinking mouth 18; air channel 19; sealing ring 20; air outlet 21; second stepped groove 22; first transparent sheet 23; second transparent sheet 24; sample target 25; spring 26; fixing piece 27; and orifice 28.

DETAILED DESCRIPTION

The present invention is further described below in combination with drawings and embodiments.

In the present embodiment, as shown in FIG. 1, a sample loading apparatus for laser ablation includes a target seat 1 and a base 2, and preferably further includes an adapter plate 3. The arrangement of the adapter plate 3 is favorable for the use and fixation of the sample loading apparatus. The target seat 1 and the base 2 are simple in structure. The replacement operation of the sample target is simple and convenient, thereby avoiding generating an abnormal instrumental analysis background due to an untight seal of sample chambers and benefiting the enhancement of long-term stability and accuracy of the operation of analytical instruments.

Figure 2:
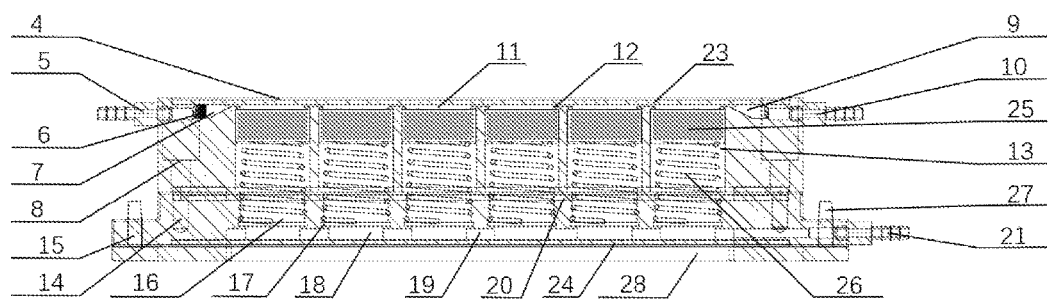
FIG. 2 is a schematic diagram of a longitudinal section structure of a sample loading state in embodiments of the present invention.
Figure 3:
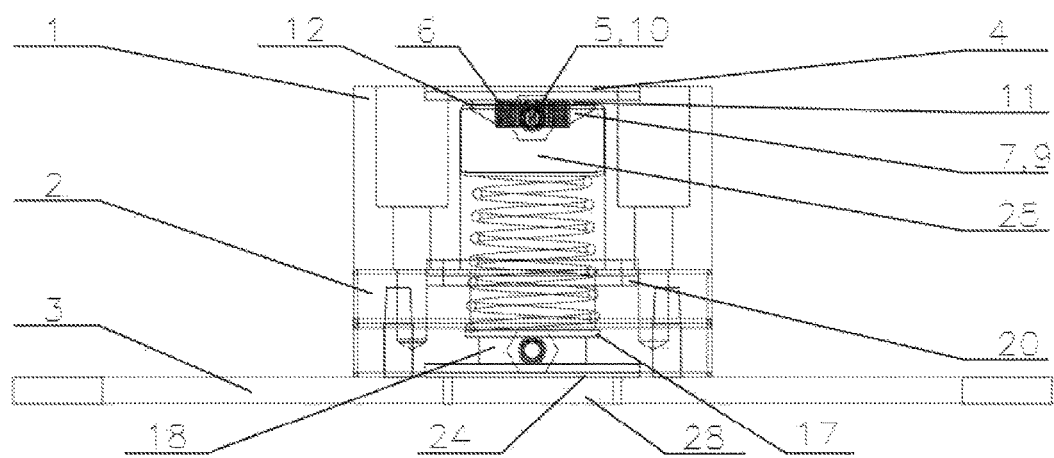
FIG. 3 is a schematic diagram of a transverse section structure of a sample loading state in embodiments of the present invention.
Figure 4:
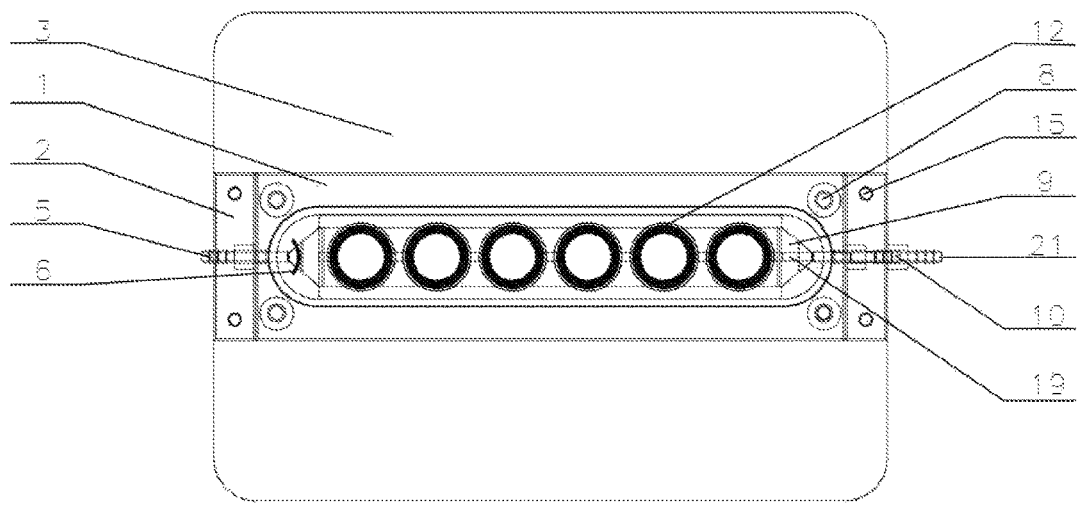
FIG. 4 is a top view of embodiments in the present invention.

With reference to FIGS. 2-4, the target seat 1 and the base 2 are connected hermetically and form an air channel 19, an aerosol channel 11 and a sample chamber. Specifically, the target seat 1 and the base 2 are preferably sealed by virtue of an O-shaped sealing ring 20, so that the sample chamber may be communicated with outside by virtue of a carrier gas inlet 5 and an exhaust port only. The exhaust port includes an aerosol outlet 10 and an air outlet 21. A stop valve is arranged at the air outlet 21 and is used for opening and closing the air outlet 21.

With reference to FIGS. 5-10, during specific implementation of the sample chamber, preferably the target seat 1 includes upper chamber bodies 13; the base 2 includes lower chamber bodies 16; fixing holes 14 with internal threads are formed in positions, which correspond to the base 2 respectively, of four corners of the target seat 1; and the target seat 1 is fixed to the base 2 by fixing pieces 8 at the fixing holes 14, so that the target seat 1 and the base 2 are hermetically connected together by virtue of the O-shaped sealing ring 20, and the upper chamber bodies 13 and the lower chamber bodies 16 correspond to one another and form the sample chambers.

A first shrinking mouth is formed in the top of each of the upper chamber bodies 13 and positioned on a lower surface of the aerosol channel 11. During specific implementation, preferably the first shrinking mouth is fixedly arranged on the top of the upper chamber body 13 by virtue of an annular blocking sheet 12, and the first shrinking mouth is formed at an opening in the middle part of the blocking sheet 12.

A spring 26 is arranged in each of the sample chambers. One end of the spring 26 is fixedly arranged at the lower chamber body 16. During specific fixation, preferably the lower chamber body 16 includes a second shrinking mouth 18. During specific implementation, preferably the spring is fixedly arranged at a lower position of the lower chamber body 16 by virtue of an annular supporting piece 17; the second shrinking mouth 18 is formed at an opening in the middle part of the annular supporting piece 17; and one end of the spring 26 may be fixed by virtue of a side wall of the lower chamber body 16 and a top wall of the supporting piece 17. The spring 26 is used for enabling a sample target 25 to be limited in the sample chamber and abutted at the first shrinking mouth. Through the arrangement of the spring 26, the sample target 25 may be directly fixed without using plasticine and the like, and a fixing effect is firm and reliable. Moreover, the sample target 25 may be constantly abutted at the first shrinking mouth. Correspondingly, the shape of the first shrinking mouth is matched with the shape of the sample target 25, so that the first shrinking mouth is constantly covered by the sample target 25. The structure may further increase the transmission efficiency of the aerosol, and avoid retention and accumulation of the aerosol, so that the analytical results are more accurate and reliable.

An opening is formed in a lower surface of the sample chamber and communicated with the air outlet 21 by virtue of the air channel 19. The structure is favorable for rapid and complete discharge of air in the sample loading apparatus before laser ablation of the sample target 25. When the sample target 25 is subjected to laser ablation, since the sample target is positioned on the upper part of the sample chamber, the lower part of the sample chamber and the air channel 19 may be used for stacking the sample target 25 and slowly-released oxygen and the like in the carrier gas, thereby reducing interference on mass spectrometric detection, benefiting the stability of baselines of partial elements in the analysis process, and benefiting the accuracy of analyzing element content and isotope ratios, so that the in-situ laser analysis conditions tend to be consistent; and therefore, the whole detection process is more stable and reliable.

The quantity of the sample chambers is preferably more than 6, and specifically preferably: $6 \leq N \leq 15$. The sample chambers are sequentially communicated in series by virtue of the air channel 19 along a direction from the carrier gas inlet 5 to the aerosol outlet 10. The structure enables the sample loading apparatus to load multiple sample targets 25 at a time, and a replacement frequency of the sample targets may be decreased, so that mass spectrometry airflow conditions are more stable because the samples can be replaced without opening the sample chambers, and the reliability of the mass spectrometry results is ensured.

The aerosol channel 11 sequentially includes a first end part 7, a middle part and a second end part 9 along the direction from the carrier gas inlet 5 to the aerosol outlet 10. The porous screen guide plate 6 is preferably arranged at the carrier gas inlet 5 and is used for guiding the carrier gas, so that airflow in the middle part of the aerosol channel 11 is uniform, thereby effectively avoiding the position effect of a sample analysis point, ensuring the analytical accuracy, avoiding generating vortex, further avoiding a severe elemental fractionation and memory effect caused by the vortex and further enhancing the consistency of the in-situ laser analysis conditions.

The aerosol channel 11 is preferably of a flat structure during specific implementation. As an example, when an actual volume of the aerosol channel 11 is 0.7 ml-4.5 ml, according to a flow rate of 800 ml/min of currently conventional laser ablation carrier gas, the flow rate is about 13.3 ml per second, and time of inner gas replacement is generally 0.06 s-0.4 s once. Calculated according to the sectional area of the aerosol channel 11 at different heights, air velocity of the carrier gas is approximately 190-32 cm/s. A larger airflow may decrease the potential risk of cross contamination among the samples due to aerosol deposition generated by the laser ablation sample targets 25. Moreover, the transmission efficiency of the aerosol is increased, the analysis efficiency and the accuracy are increased, and the consistency of the in-situ laser analysis conditions is further enhanced. Therefore, preferably, after the sample targets 25 are completely loaded, a height from a top surface of the aerosol channel 11 to the upper surfaces of the sample targets 25 is preferably: $0.5 \text{ mm} \leq H \leq 3.0 \text{ mm}$. Correspondingly, the volume V of the aerosol channel is preferably 0.7 ml<V<5 ml, and the sectional area S of the aerosol channel is preferably $0 \text{ cm}^2 < S < 0.5 \text{ cm}^2$. During specific implementation, the middle part of the aerosol channel 11 is preferably in the shape of a flat cuboid. The structure may further increase the transmission efficiency.

Figure 5:
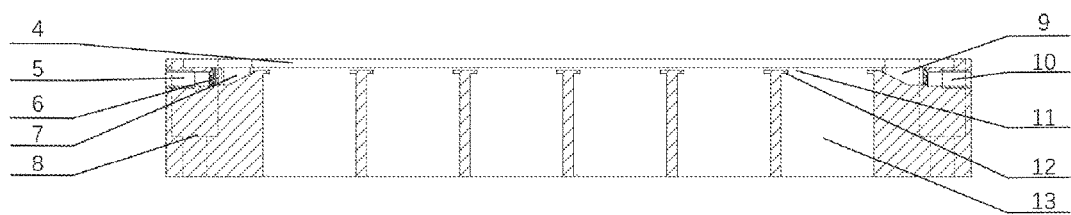
FIG. 5 is a schematic diagram of a longitudinal section structure of a target seat in FIG. 1.
Figure 6:
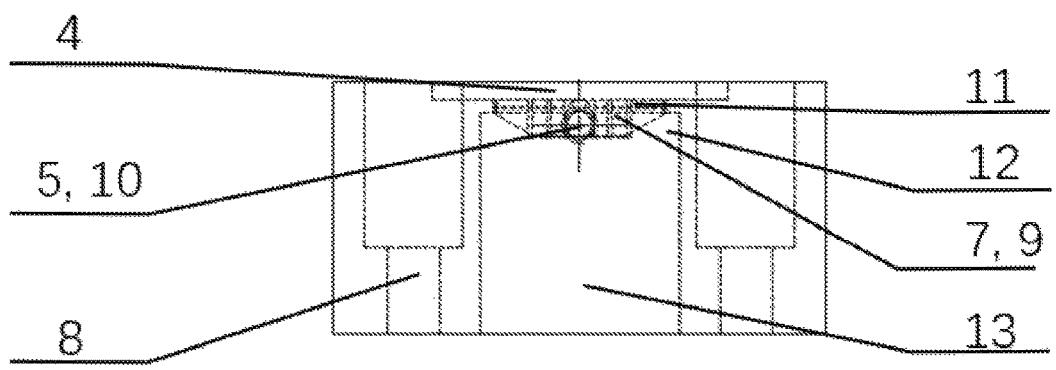
FIG. 6 is a schematic diagram of a transverse section structure of a target seat in FIG. 1.
Figure 7:
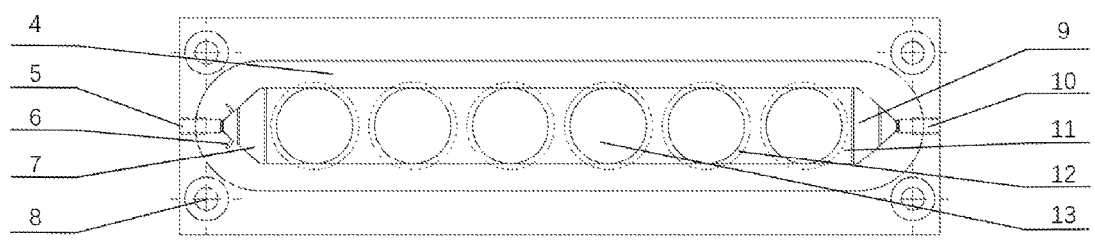
FIG. 7 is a top view of a target seat in FIG. 1.

During specific implementation, with reference to FIGS. 5-7, the target seat 1 preferably includes the carrier gas inlet 5, the aerosol channel 11 and the aerosol outlet 10. The carrier gas inlet 5 and the aerosol outlet 10 are preferably positioned on two opposite side surfaces of the target seat 1 respectively. One end of the aerosol channel 11 is communicated with the carrier gas inlet 5, and the other end of the aerosol channel 11 is communicated with the aerosol outlet 10. The top of the aerosol channel 11 includes the first transparent material, so that the laser transmits from the top of the aerosol channel by virtue of the first transparent material and ablates the sample target 25. During specific implementation, the target seat 1 includes a first transparent sheet 23 and a first stepped groove 4. The first stepped groove 4 is formed in the top surface of the target 1; the first transparent sheet 23 is seamlessly adhered to a notch of the first stepped groove 4 hermetically by virtue of special glue and formed by the first transparent material; and the first transparent material includes fluorite glass or UV transparent quartz glass. When the first transparent sheet 23 is formed by the UV transparent quartz glass, preferably the surface of the first transparent sheet 23 includes a laser antireflection film coating. The structure may increase transmittance of the laser, so that the laser ablation is more efficient and energy-saving, and the effect is better.

Figure 8:
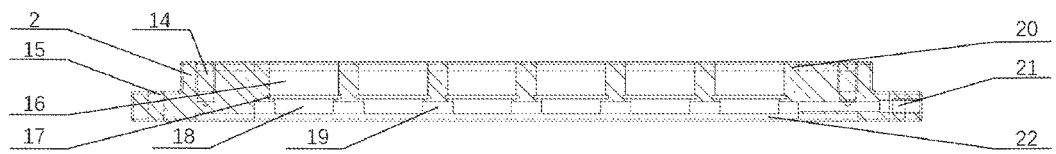
FIG. 8 is a schematic diagram of a longitudinal section structure of a base in FIG. 1.
Figure 9:
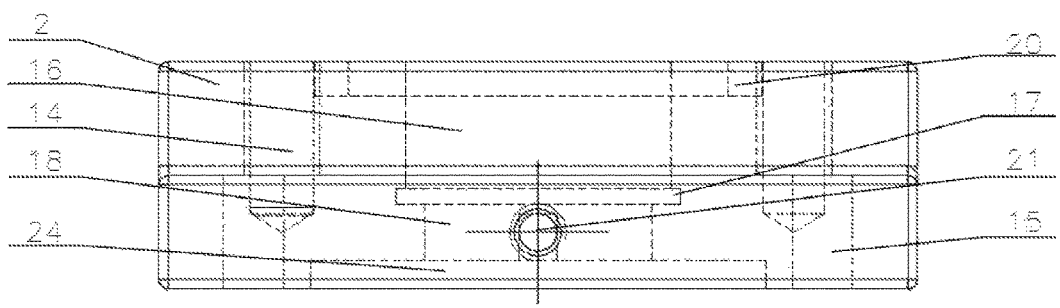
FIG. 9 is a schematic diagram of a transverse section structure of a base in FIG. 1.
Figure 10:
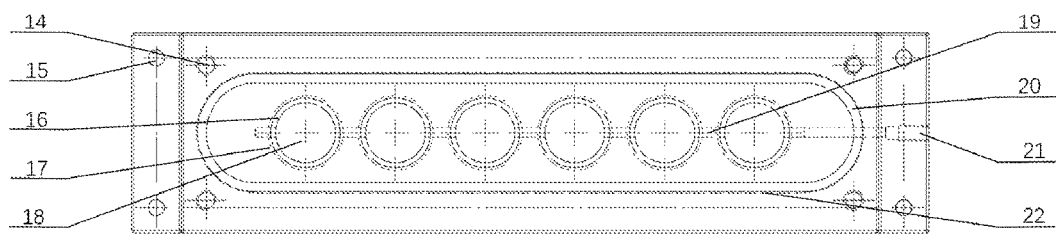
FIG. 10 is a top view of a base in FIG. 1.

During specific implementation, with reference to FIGS. 8-10, the base 2 preferably includes a second transparent sheet 24 and a second stepped groove 22. The second stepped groove 22 is formed in a bottom surface of the base 2; the second transparent sheet 24 is seamlessly adhered to a notch of the second stepped groove 22 hermetically by virtue of the special glue; the air channel 19 is positioned in the base 2; and the air outlet 21 is positioned in a side surface of the base.

Through the arrangement of the first transparent sheet 23 and the second transparent sheet 24, internal structures of the samples may be directly observed from an upper side by utilizing reflected light, and may also be observed from a lower side by utilizing transmitted light.

During specific implementation of the adapter plate 3, an orifice 28 is formed in a position corresponding to the second transparent sheet 24 in a penetrating manner; fixing holes 15 are formed in four corners of the base 2; and the base 2 is fixed to the adapter plate 3 by fixing pieces 27 at the fixing holes 15. The structure increases compatibility of the sample loading apparatus.

During specific implementation, the sample targets 25 include conventional monominerals, glass, solid chips, etc. When the first shrinking mouth is circular, the sample targets 25 are circular, or special-shaped targets are put by changing the shape of the first shrinking mouth. The present invention may be applied to an existing mainstream laser ablation in-situ analysis instrument, and may realize in-situ micro analysis of the content of primary trace elements and isotope compositions in the monominerals such as zircon, pyroxene, olivine, garnet, monazite, sphene, apatite and the like, as well as materials, frozen biological tissues, archaeological samples, glass and other solid samples.

During use, the target seat 1 is disassembled from the base 2 and placed on a clean workbench; all samples (such as the zircon and other monominerals) are made into the sample targets 25 with a diameter of 16 mm; the sample targets 25 are placed in the sample chambers in a direction that a polished surface of a to-be-analyzed mineral is upward; the target seat 1 is mounted above the base 2; and the sample targets 25 are automatically compacted by the springs 26 to achieve a fixing effect; the target seat 1 and the base 2 are fixed by screws or clamping seats, and then the base 2 is mounted on the adapter plate 3; the target seat 1 and the base 2 are sealed by an O-shaped ring or other sealing devices; and a carrier gas inlet path is connected to the carrier gas inlet 5; the aerosol outlet 10 is connected to a mass spectrometer by a pipeline; and a stop valve closing gas path is arranged at the air outlet 21 of the base 2. During operation, firstly the aerosol outlet 10 is closed; the stop valve of the air outlet 21 is opened; the carrier gas (such as helium) is introduced at the carrier gas inlet 5 for 10-20 min to fully discharge the air in channels of the target seat 1 and the base 2 and in the sample chambers so as to fully decrease or remove the interference caused by the oxygen and nitrogen; and then the aerosol outlet 10 is opened, the stop valve is closed, and purging is continued for 5 min, thereby completing the replacement of the sample targets 25.

It should be understood that, those ordinary skilled in the art may make improvements or transformations according to the above description, while all the improvements and transformations should belong to a protection scope of claims in the present invention.

The patent for the present invention is illustratively described above. Apparently, implementation of the patent for the present invention is not limited by the above manner. Various improvements made according to methodological concepts and technical solutions in the patent for the present invention or concepts and technical solutions in the patent for the present invention which are directly applied to other occasions without any improvement should be included in the protection scope of the present invention.

What is claimed is:

1. A sample loading apparatus for laser ablation, comprising a sample chamber, a carrier gas inlet and a gas outlet and further comprising a target seat and a base, wherein the gas outlet includes an air outlet and an aerosol outlet; the target seat and the base are connected hermetically and form an air channel, an aerosol channel and a sample chamber, wherein
   a shrinking mouth is formed in the top of the sample chamber and positioned in a lower surface of the aerosol channel;
   a spring is arranged in the sample chamber and is used for enabling a sample target to be limited in the sample chamber and abutted at the shrinking mouth;
   an opening is formed in a lower surface of the sample chamber and communicated with the air outlet by virtue of the air channel;
   a stop valve is arranged at the air outlet and is used for opening and closing the air outlet; and
   one end of the aerosol channel is communicated with the carrier gas inlet, and the other end of the aerosol channel is communicated with the aerosol outlet; and the top of the aerosol channel includes a first transparent material, so that laser transmits from the top of the aerosol channel by virtue of the first transparent material and ablates the sample target.

2. The sample loading apparatus according to claim 1, wherein a porous screen guide plate is arranged at the carrier gas inlet, for guiding the carrier gas.

3. The sample loading apparatus according to claim 1, wherein a blocking sheet is arranged on the top of the sample chamber, and an opening is formed in the middle part of the blocking sheet to form the shrinking mouth.

4. The sample loading apparatus according to claim 1, wherein the carrier gas inlet and the aerosol outlet are respectively positioned on two opposite side surfaces of the target seat, the aerosol channel is positioned in the target seat, and a middle part of the aerosol channel is in the shape of a flat cuboid.

5. The sample loading apparatus according to claim 1, wherein the target seat includes an upper chamber body; the base includes a lower chamber body; one end of the spring is fixedly arranged on the lower chamber body; the target seat and the base are sealed by an O-shaped sealing ring; and the upper chamber body and the lower chamber body correspond to each other and form the sample chamber.

6. The sample loading apparatus according to claim 1, wherein the target seat includes a first transparent sheet and a first stepped groove; the first stepped groove is formed in a top surface of the target seat; the first transparent sheet is hermetically arranged at a notch of the first stepped groove; the first transparent sheet is formed by the first transparent material; and the first transparent material includes fluorite glass or UV transparent quartz glass.

7. The sample loading apparatus according to claim 1, wherein the base includes a second transparent sheet and a second stepped groove; the second stepped groove is formed in a bottom surface of the base; the second transparent sheet is hermetically arranged at a notch of the second stepped groove; the air channel is positioned in the base; and the air outlet is positioned in a side surface of the base.

8. The sample loading apparatus according to claim 1, wherein a volume of the aerosol channel is: 0 ml<V<5 ml; the sectional area of the aerosol channel is: 0 cm$^2$<S<0.5 cm$^2$; and a height from the top surface of the aerosol channel to the upper surface of the sample target is: 0.5 mm≤H≤3.0 mm.

9. The sample loading apparatus according to claim 1, wherein a shape of the shrinking mouth is matched with a shape of the sample target, so that the shrinking mouth is covered by the sample target.

10. The sample loading apparatus according to claim 1, wherein a quantity of the sample chambers is: 6≤N≤15, and the sample chambers are communicated in series by virtue of air channels.

\* \* \* \* \*